United States Patent
Eskuchen et al.

(10) Patent No.: US 8,357,381 B2
(45) Date of Patent: Jan. 22, 2013

(54) DISPERSIONS COMPRISING ACYLGLUTAMATES

(75) Inventors: Rainer Eskuchen, Langenfeld (DE); Caroline Goget, Paris (FR); Rolf Kawa, Monheim (DE)

(73) Assignee: Cognis IP Management GmbH, Duesseldorf (DE)

( * ) Notice: Subject to any disclaimer, the term of this patent is extended or adjusted under 35 U.S.C. 154(b) by 609 days.

(21) Appl. No.: 12/298,687

(22) PCT Filed: Apr. 18, 2007

(86) PCT No.: PCT/EP2007/003392
§ 371 (c)(1),
(2), (4) Date: Oct. 27, 2008

(87) PCT Pub. No.: WO2007/124864
PCT Pub. Date: Nov. 8, 2007

(65) Prior Publication Data
US 2009/0258043 A1    Oct. 15, 2009

(30) Foreign Application Priority Data
Apr. 27, 2006 (EP) .................................... 06008764

(51) Int. Cl.
*A61K 9/127* (2006.01)
(52) U.S. Cl. ........................................ 424/401; 424/415
(58) Field of Classification Search ........................ None
See application file for complete search history.

(56) References Cited

U.S. PATENT DOCUMENTS

| | | | |
|---|---|---|---|
| 6,407,247 | B1 | 6/2002 | Habeck et al. |
| 6,623,746 | B1 | 9/2003 | Wadle |
| 7,179,880 | B2 | 2/2007 | Kawa |
| 2002/0034480 | A1* | 3/2002 | Grimm et al. ................... 424/63 |
| 2005/0025957 | A1 | 2/2005 | Issberner |
| 2005/0238610 | A1 | 10/2005 | Nielsen et al. |

FOREIGN PATENT DOCUMENTS

| | | |
|---|---|---|
| WO | 00/04230 A1 | 1/2000 |
| WO | 03/041676 A1 | 5/2003 |

OTHER PUBLICATIONS

Takehara, M., et al., "Surface Active N-Acylglutamate: II. Physicochemical Properties of Long Chain N-Acylglutamic Acids and Their Sodium Salts" Mar. 1972, vol. 49, pp. 143-150 Journal of the American Oil Chemists' Society.
European Search Report, Appln. No. 11154398-9, May 30, 2011.
Finkel, P., "Formulierung kosmetischer Sonnenschutzmittel", Mar. 1999, pp. 10-16 Parfumerie und Kosmetik, 80, Jahrgang, Nr. Mar. 1999, With machine translation of abstract.
Finkel, P., "Formulierung kosmetischer Sonnenschutzmittel", Aug. 1996, pp. 543-548 SOFW-Journal, 122 Jahrgang Aug. 1996, See English abstract.

* cited by examiner

*Primary Examiner* — Sreeni Padmanabhan
*Assistant Examiner* — Svetlana M Ivanova
(74) *Attorney, Agent, or Firm* — Diehl Servilla LLC

(57) ABSTRACT

The invention relates to dispersions comprising water, lipophilic phase and emulsifier, characterized in that the emulsifier is preferably present in an amount of less than or equal to about 3% by weight based on the total weight of the dispersion, and in that the emulsifier comprises at least one acylglutamate. Preferred dispersions of the invention are suitable for cosmetic and/or pharmaceutical preparations.

11 Claims, No Drawings

DISPERSIONS COMPRISING ACYLGLUTAMATES

CROSS REFERENCE TO RELATED APPLICATIONS

This application is the National Phase entry of PCT/EP2007/003392, filed Apr. 18, 2007, which claims priority to EPO patent application number 06008764.0 filed Apr. 27, 2006, both of which are incorporated herein by reference in their entireties.

FIELD OF THE INVENTION

The invention is in the field of dispersions and relates to finely divided, particularly storage-stable, dispersions comprising acylglutamates.

BACKGROUND OF THE INVENTION

The prior art describes a multiplicity of cosmetic emulsions with a multiplicity of highly diverse emulsifiers. Thus, for example, EP 1 502 644 A2 describes emulsifier combinations which are free from ethoxylated emulsifiers and comprise alkyl oligoglucosides, polyol polyhydroxystearates and acylglutamates and are suitable for the preparation of nanoemulsions. The emulsions described in EP 1 502 644 all comprise total emulsifier amounts of more than 3% by weight.

The object of the present invention was to provide storage-stable dispersions with the lowest possible fraction of emulsifier. Of particular interest was the phase stability, especially during storage at elevated temperatures, and at the same time high sensory performance (softness, care) of the dispersion. Furthermore, it was desired that large amounts of lipophilic phase relative to the total amount of emulsifier can be incorporated to give a stable dispersion. It was also an object of the invention that the dispersion can be diluted while retaining the particle size distribution of the dispersion.

Surprisingly, it has been found that dispersions which comprise the emulsifier in an amount of less than or equal to 3% by weight, based on the total weight of the dispersion, and also comprise at least one acylglutamate as emulsifier achieve this object. The dispersions according to the invention are storage-stable, have excellent sensory properties with regard to care and softness, and permit the incorporation of large amounts of lipophilic phase. The dispersions according to the invention exhibit no phase separation, particularly upon storage at elevated temperatures over a period of several weeks. Furthermore, the dispersions according to the invention can be diluted without changing the particle size distribution of the dispersion.

DETAILED DESCRIPTION OF PREFERRED EMBODIMENTS

The invention relates to dispersions comprising water, lipophilic phase and emulsifier, characterized in that the emulsifier is present in an amount of less than or equal to 3% by weight, based on the total weight of the dispersion, and in that the emulsifier comprises at least one acylglutamate.

Dispersions

Dispersion is the term used to refer to a system (disperse system) of two or more phases, one of which is continuous (dispersant) and at least one other of which is finely divided (dispersed phase). Examples of dispersions are: emulsions (dispersant and dispersed phase: liquid phases insoluble in one another), aerosols [dispersant gaseous, dispersed phase liquid (=mist) or solid (=smoke, dust)], suspensions (dispersant liquid, dispersed phase solid).

Unless stated otherwise, all of the % by weight data are based on the total weight of the dispersion.

Acylglutamates

Acylglutamates are known emulsifiers which conform to the formula (I)

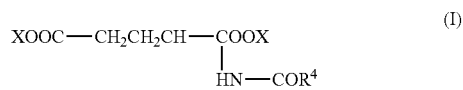

in which $R^4CO$ is a linear or branched acyl radical having 6 to 22 carbon atoms and 0, 1, 2 or 3 double bonds and X is hydrogen, an alkali metal and/or alkaline earth metal, ammonium, alkylammonium, alkanolammonium or glucammonium. Their preparation takes place, for example, through Schotten-Baumann acylation of glutamic acid with fatty acids, fatty acid esters or fatty acid chlorides. Commercial products are obtained, for example, from Hoechst AG, Frankfurt/DE or Ajinomoto Co. Inc., Tokyo/JP. An overview of the preparation and properties of acylglutamates is given by M. Takehara et al. in J. Am. Oil Chem. Soc. 49 (1972) 143. Typical examples of suitable acylglutamates which are suitable within the context of the invention are those acylglutamates which are derived from fatty acids having 6 to 22 and preferably 12 to 18 carbon atoms. Particular preference is given to acylglutamates which are derived from fatty acids having 16 to 18 carbon atoms, in particular from fatty acids having 18 carbon atoms (stearoylglutamates). Particular preference is given to coconut fatty acid glutamates, for example $C_{12/14}$- or $C_{12/18}$-coconut fatty acid. In particular, the mono- or dialkali metal salts of the acylglutamate are used. Particular preference is given to sodium salts of stearoylglutamate (INCI: Sodium Stearoyl Glutamate), as are sold, for example, under the trade name Eumulgin® SG (Cognis Deutschland GmbH & Co. KG), or Amisoft HS-11P (Ajinomoto, USA).

The terms acylglutamate and acylglutamates used within the context of the invention include both individual acylglutamates and also any desired mixtures of different acylglutamates.

Emulsifier

Within the context of the invention, emulsifiers are understood as meaning those substances which have a HLB value of greater than or equal to 10, preferably greater than or equal to 12.

The dispersions according to the invention comprise less than 3% by weight of emulsifier, based on the total amount of the dispersion. In a preferred embodiment of the invention, the emulsifier comprises more than 30% by weight, preferably more than 50% by weight, of acylglutamates. In a preferred embodiment, the emulsifier comprises more than 60% by weight, in particular more than 70% by weight, preferably more than 80% by weight, preferably more than 90% by weight, of acylglutamates. In one embodiment of the invention, the emulsifier consists of 100% of acylglutamates.

If the dispersions comprise phospholipids, these are not included in the emulsifiers.

A high fraction in the emulsifier of acylglutamates has proven particularly advantageous for the storage stability of the dispersions.

Besides the acylglutamates, the dispersions according to the invention can comprise customary further emulsifiers or surfactants. The selection is expediently governed according to the intended use of the dispersion and in particular according to the type of lipophilic phase which is to be emulsified. At least one nonionic emulsifier is preferably present as further emulsifiers. Examples of nonionic emulsifiers which may be mentioned are alkyl oligoglycosides, polyol polyhydroxystearates and also sorbitan mono- or diesters.

At least one anionic emulsifier is preferably present as further emulsifiers.

In a preferred embodiment of the invention, the dispersions comprise less than 2.5% by weight, in particular less than 2% by weight, preferably less than 1% by weight, of emulsifier.

In a preferred embodiment of the invention, the dispersions comprise less than 2.5% by weight, in particular less than 2% by weight, preferably less than 1% by weight, of emulsifier, where the emulsifier in each case comprises more than 30% by weight, preferably more than 50% by weight, of acylglutamates, preferably more than 60% by weight, in particular more than 70% by weight, preferably more than 80% by weight, preferably more than 90% by weight, of acylglutamates.

In a preferred embodiment of the invention, the emulsifier comprises less than 10% by weight, preferably less than 5% by weight, of ethoxylated emulsifiers, in particular less than 2% by weight of ethoxylated emulsifiers. In a preferred embodiment of the invention, the dispersions comprise no ethoxylated emulsifiers.

One embodiment of the invention covers dispersions characterized in that the emulsifier is present in an amount of less than or equal to 3% by weight, based on the total weight of the dispersion, and in that the emulsifier comprises at least one acylglutamate and in that the emulsifier comprises less than 10% by weight of ethoxylated emulsifiers.

One embodiment of the invention covers dispersions characterized in that the emulsifier is present in an amount of less than or equal to 3% by weight, based on the total weight of the emulsion, and in that the emulsifier comprises more than 30% by weight, preferably more than 50% by weight, of acylglutamates, and in that the emulsifier comprises less than 10% by weight of ethoxylated emulsifiers.

Further Emulsifiers

Customary further emulsifiers which may be mentioned are the following substances provided they have a HLB value of greater than or equal to 10, preferably greater than or equal to 12.

Cetyl dimethicone copolyol (e.g. Abil EM-90), polyglyceryl-2 dipolyhydroxystearate (e.g. Dehymuls PGPH), polyglycerol-3 diisostearate (e.g. Lameform TGI), polyglyceryl-4 isostearate (e.g. Isolan GI 34), polyglyceryl-4 diisostearate/polyhydroxystearate/sebacate (Isolan GPS), polyglyceryl-3 oleate, diisostearoyl polyglyceryl-3 diisostearate (e.g. Isolan PDI), polyglyceryl-3 methylglucose distearate (e.g. Tego Care 450), polyglyceryl-3 beeswax (e.g. Cera bellina), polyglyceryl-4 caprate (e.g. polyglycerol caprate T2010/90), polyglyceryl-3 cetyl ether (e.g. Chimexane NL), polyglyceryl-3 distearate (e.g. Cremophor GS 32) and polyglyceryl polyricinoleate (e.g. Admul WOL 1403), glyceryl oleate (e.g. Monomuls 90-O 18), alkyl glucosides (e.g. Plantacare 1200, Emulgade PL 68/50, Montanov 68, Tego Care CG 90, Tego Glucoside L 55), methyl glucose isostearate (e.g. Tego Care IS), methyl glucose sesquistearate (Tego Care PS), sodium cocoyl hydrolyzed wheat protein (e.g. Gluadin WK), alkali metal salts of alkyl phosphates (e.g. Amphisol K, Crodafos CKP), sodium alkylsulfates (e.g. Lanette E), sucrose esters (e.g. Crodesta F-10, F-20, F-50, F-70, F-110, F-160, SL-40, Emulgade Sucro), ethoxylated and/or propoxylated fatty alcohols, fatty acids, castor oils and hydrogenated castor oils (e.g. Eumulgin B1, B2, B3, L, HRE 40, HRE 60, RO 40 Cremophor HRE 40, HRE 60, L, WO 7, Dehymuls HRE 7, Arlacel 989), PEG-30 dipolyhydroxystearate (Dehymuls LE, Arlacel P 135), sorbitan ester, sorbitan ester ethoxylated and/or propoxylated, and mixtures thereof.

Suitable further emulsifiers are, for example, nonionic emulsifiers from at least one of the following groups:
- alkyl and/or alkenyl oligoglycosides having 8 to 22 carbon atoms in the alk(en)yl radical
- mono-, di- and trialkyl phosphates, and also mono-, di- and/or tri-PEG-alkyl phosphates and salts thereof;
- wool wax alcohols;
- polysiloxane-polyalkyl-polyether copolymers and corresponding derivatives;
- block copolymers, e.g. polyethylene glycol-30 dipolyhydroxy stearate;
- polymer emulsifiers, e.g. pemulen grades (TR-1, TR-2) from Goodrich;
- polyalkylene glycols, and
- glycerol carbonate.

Alkyl and/or Alkenyl Oligoglycosides

Alkyl and/or alkenyl oligoglycosides, their preparation and their use are known from the prior art. Their preparation takes place in particular by reacting glucose or oligosaccharides with primary alcohols having 8 to 18 carbon atoms. As regards the glycoside radical, either monoglycosides in which a cyclic sugar radical is glycosidically bonded to the fatty alcohol, or else oligomeric glycosides with a degree of oligomerization up to preferably about 8 are suitable. The degree of oligomerization here is a statistical average value which is based on a homolog distribution customary for such technical-grade products.

Phospholipids

In a preferred embodiment of the invention, the dispersion furthermore comprises at least one phospholipid.

Commercially available "phospholipids" are usually complex mixtures which, depending on the origin and recovery method, can additionally comprise stearols, oils etc.

Phospholipids are complex lipids in which one of the primary hydroxyl groups of the glycerol is esterified with phosphoric acid, which in turn is esterified. The 2 other hydroxyl groups of the glycerol are esterified with long-chain, saturated or unsaturated fatty acids.

Phospholipids are phosphoric acid di- or monoesters which, on account of their fat-like solubility properties due to the lipophilic and hydrophilic components, are regarded as types of lipids and, within the organism, are involved as membrane lipids in the construction of layer structures, the membranes. Phosphatidic acids are glycerol derivatives which are esterified in the 1-sn and 2 position with fatty acids (1-sn position: mostly saturated, 2 position: mostly mono- or polyunsaturated), but are esterified on atom 3-sn with phosphoric acid and are characterized by the general structural formula

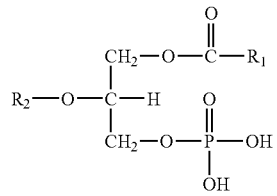

In the phosphatidic acids occurring in human or animal tissue, the phosphate radical is in most cases esterified with amino alcohols such as choline (lecithin=3-sn-phosphatidylcholine) or 2-aminoethanol (ethanolamine) or L-serine (cephalin=3-sn-phosphatidylethanolamine or sn-phosphatidyl-L-serine), with myo-inositol to give the phosphoinositides common in tissues [1-(3-sn-phosphatidyl)-D-myo-inosites], with glycerol to give phosphatidylglycerols.

Lecithins are characterized by the general structural formula

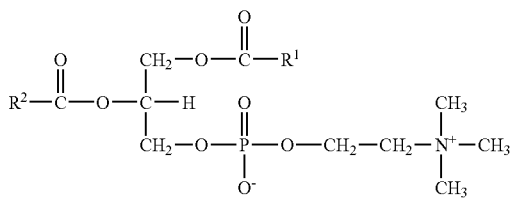

where $R^1$ and $R^2$ are typically unbranched aliphatic radicals having 15 or 17 carbon atoms and up to 4 cis double bonds.

Cardiolipins (1,3-bisphosphatidylglycerols) are phospholipids of two phosphatidic acids linked via glycerol. Lysophospholipids are obtained if an acyl radical is cleaved off from phospholipids by phospholipase A (e.g. lysolecithins).

Lysophospholipids are characterized by the general structural formula

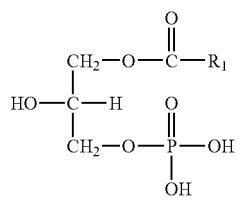

Lysolecithins, for example, are characterized by the general structural formula

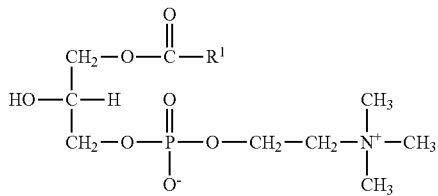

where $R^1$ and $R^2$ are typically unbranched aliphatic radicals having 15 or 17 carbon atoms and up to 4 cis double bonds.

The phospholipids also include plasmalogens in which, instead of a fatty acid, an aldehyde (in the form of an enol ether) is bonded in the 1 position; the O-1-sn-alkenyl compounds corresponding to the phosphatidyl-cholines, for example, are called phosphatidalcholins.

The basic structure of the phosphosphingolipids is sphingosine or phytosphingosine, which are characterized by the following structural formulae:

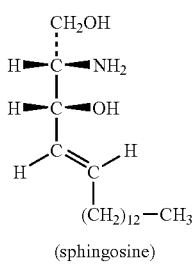 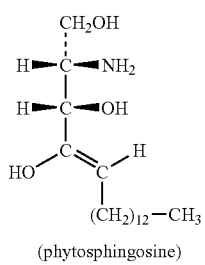

(sphingosine)   (phytosphingosine)

Modifications of sphingolipids are characterized, for example, by the general basic structure

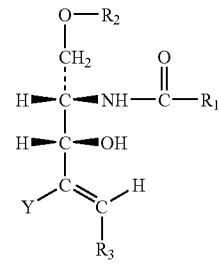

in which $R_1$ and $R_3$, independently of one another, are saturated or unsaturated, branched or unbranched alkyl radicals having 1 to 28 carbon atoms, $R_2$ is selected from the group: hydrogen atom, saturated or unsaturated, branched or unbranched alkyl radicals having 1 to 28 carbon atoms, sugar radicals, phosphate groups which are unesterified or esterified with organic radicals, sulfate groups that are unesterified or esterified with organic radicals, and Y is either a hydrogen atom, a hydroxy group or another heterofunctional radical.

Sphingophospholipids:

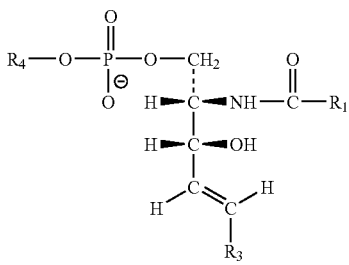

$R_1$ and $R_3$ are alkyl radicals, $R_4$ is an organyl radical. Sphingomyelins are organylphosphorylated sphingolipids of the type

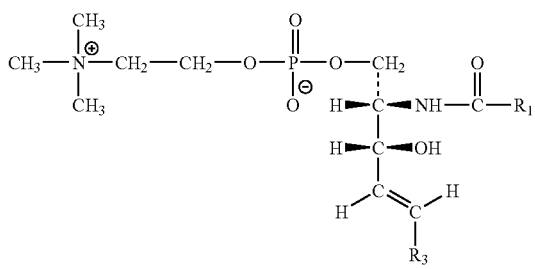

Within the context of this invention, the term phospholipids also includes phosphosphingolipids and sphingophospholipids.

In a preferred embodiment of the invention, phospholipids of vegetable origin are used. These can be obtained, for example, from soya or other vegetable seed cells.

Phospholipids to be used advantageously are selected from phospholipids which have been deoiled and/or fractionated and/or spray-dried and/or acetylated and/or hydrolyzed and/or hydrogenated.

Phospholipids to be used advantageously are selected from phospholipids which are phosphatidylcholin enriched and/or phosphatidylinositol enriched.

Phospholipids to be used advantageously according to the invention are commercially available, for example, under the trade names Leciprime 1800 IP (Cargill), Phosal 50 SA+ (Phospholipid), Soluthin MD (Phospholipid), Lipoid SL 80-3 (Lipoid).

The amount of phospholipids (one or more compounds) in the emulsions is preferably 0.01 to 10% by weight, particularly preferably 0.1-8% by weight, in particular 0.5-5% by weight, in particular 2 to 4% by weight, based on the total weight of the emulsion.

Dispersions

One parameter for describing dispersions or the size distribution of the dispersed particles is the Sauter diameter. The Sauter diameter is defined as the diameter of a drop with the same ratio of drop volume to drop surface area as is present as the average value in the overall dispersion.

The Sauter diameter is defined mathematically as D[3,2]:

$$D[3,2] = \bar{d}_m = \frac{\sum s_i d_i}{S} = \frac{\sum n_i d_i^3}{\sum n_i d_i^2}$$

Where $s_i$ is the total surface area, $n_i \pi d_i^2$ of the particles is within the group i and S is the total surface area of the entire population.

In a preferred embodiment of the invention, the Sauter diameter $d_{3,2}$ of the dispersion is less than or equal to 400 nm, in particular less than or equal to 200 nm.

One parameter for describing dispersions (in particular emulsions) or the size distribution of the dispersed particles is the width of the droplet size distribution. The width of the droplet size distribution can be described by the so-called WDS value:

$$WDS = \frac{d_{3,90} - d_{3,10}}{d_{3,50}}$$

d droplet diameter
$d_{3,90}$ 90% of the volume of the disperse phase is formed by drops where $d \leq d_{3,90}$
$d_{3,50}$ 50% of the volume of the disperse phase is formed by drops where $d \leq d_{3,50}$
$d_{3,10}$ 10% of the volume of the disperse phase is formed by drops where $d \leq d_{3,10}$.

The lower the WDS value, the more narrow the droplet size distribution.

Preferably, the dispersions according to the invention have a WDS value of less than or equal to 2, in particular less than or equal to 1.

Lipophilic Phase

The dispersions according to the invention comprise a lipophilic phase. The lipophilic phase can comprise oil components, fats, waxes and any desired mixtures thereof.

In a preferred embodiment of the invention, the dispersion comprises 1 to 80% by weight, preferably 10 to 80% by weight, in particular 20 to 70% by weight, preferably 30 to 60% by weight, of lipophilic phase.

The dispersions according to the invention can be in the form of suspensions and/or emulsions depending on the choice of lipophilic phase. This can take place by combining various fats, oils and waxes or by the lipophilic phase consisting exclusively of one oil.

In a preferred embodiment of the invention, the lipophilic phase comprises not more than 25% by weight, preferably not more than 20% by weight (based on the total lipophilic phase) of lipophilic phase with a polarity index of greater than or equal to 35 mN/m and/or a polarity index of less than or equal to 7 mN/m. The polarity index of a lipophilic phase can be determined using a ring tensiometer (e.g. Krüss K 10), which measures the interfacial energy, which is the interfacial tension in mN/M. The lower value is 5 mN/m. This method is suitable for liquids of low viscosity provided an interface is present, i.e. the liquids are immiscible. The polarity of the lipophilic phase is determined against water. A method of measuring the interfacial tension is described in ASTM method D971-99a (reapproved 2004).

The polarity of various lipophilic phases is described, for example, in DE 1020004003436 A1 on pages 8 to 11, to which reference is expressly made here.

In one embodiment of the invention, the lipophilic phase comprises at least one oil.

The term "oils" (used synonymously: oil component) is used to refer to water-insoluble organic compounds that are liquid at 30° C. and have a relatively low vapor pressure. The common feature of the oils is not their corresponding chemical constitution, but their similar physical consistency.

Suitable oil components are, for example, the compound classes specified below provided these are liquid at 30° C. Thus, for example, Guerbet alcohols based on fatty alcohols having 6 to 18, preferably 8 to 10, carbon atoms (e.g. Eutanol® G), esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_3$-$C_{38}$-alkylhydroxycarboxylic acids with linear or branched $C_6$-$C_{22}$-fatty alcohols—in particular dioctyl malate—, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, such as, for example, 1,3-dialkylcyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols (Hydagen® HSP, Sovermol® 750, Sovermol® 1102), silicone oils (cyclomethicones, silicon methicone grades etc. and/or aliphatic or naphthenic hydrocarbons, such as, for example, mineral oil, vaseline, petrolatum, squalane, squalene or dialkylcyclohexanes.

Besides dimethylpolysiloxanes, methylphenylpoly-siloxanes and cyclic silicones, suitable silicone oils are amino-, fatty-acid-, alcohol-, polyether-, epoxy-, fluorine-, glycoside- and/or alkyl-modified silicone compounds, which may be in liquid or resin form at room temperature. Also suitable are simethicones, which are mixtures of dimethicones with an average chain length of from 200 to 300 dimethylsiloxane units and silicon dioxide or hydrogenated silicates.

Suitable oil bodies are also polycarbonates, as are described, for example, in WO 03/041676, to which reference is expressly made here.

A particularly suitable polycarbonate is that known under the INCI name Hydrogenated Dimer Dilinoleyl/Dimethylcarbonate Copolymer, which is commercially available as Cosmedia® DC from Cognis Deutschland GmbH & Co. KG.

Dialkyl ethers, dialkyl carbonates, triglyceride mixtures and esters of C8-C24-fatty acids and C8-C24 fatty alcohols, polycarbonates and a mixture of these substances are particularly well suited according to the invention as oil bodies. The dialkyl carbonates and dialkyl ethers may be symmetrical or asymmetrical, branched or unbranched, saturated or unsaturated and can be prepared by reactions which are sufficiently known from the prior art. According to the invention, it is preferred to use a mixture of oil bodies which comprises esters, dialkyl ethers and triglycerides. According to the invention, it is also possible to use, inter alia, hydrocarbons, preferably with a chain length of 8 to 40 carbon atoms. They may be branched or unbranched, saturated or unsaturated. Among these, branched, saturated C8-C40-alkanes are preferred. It is possible to use either pure substances or substance mixtures. They are usually substance mixtures of different isomeric compounds. Compositions which have alkanes having 10 to 30, preferably 12 to 20, and particularly preferably 16 to 20, carbon atoms are particularly suitable and, among these, a mixture of alkanes which comprises at least 10% by weight of branched alkanes based on the total amount of the alkanes. They are preferably branched, saturated alkanes. Mixtures of alkanes which comprise more than 1% by weight of 5,8-diethyldodecane and/or more than 1% by weight of didecene are particularly well suited.

In one embodiment of the invention, the lipophilic phase comprises at least one wax.

The term wax (used synonymously: wax component) is usually understood as meaning all natural or synthetically obtained substances and substance mixtures with the following properties: they are of solid to brittly hard consistency, coarse to finely divided, transparent to opaque and melt above 30° C. without decomposition. They are of low viscosity and non-thread-drawing even a little above the melting point and exhibit a heavily temperature-dependent consistency and solubility. According to the invention, it is possible to use a wax component or a mixture of wax components which melt at 30° C. or above.

In a preferred embodiment, the lipophilic phase comprises at least one hydrophilic wax. Hydrophilic waxes are characterized by a melting point of above 30° C. and the presence of at least one functional OH group. As a distinction from the emulsifiers, hydrophilic waxes have a HLB value of less than 10.

In one preferred embodiment, the lipophilic phase comprises, as hydrophilic wax, at least one partial ester of C12 to C22 fatty acids with polyhydric alcohols.

The polyhydric alcohols which are suitable here preferably have 2 to 15 carbon atoms and at least two hydroxyl groups. The polyols can also comprise further functional groups, in particular amino groups, and/or be modified with nitrogen. Typical examples are:
  glycerol
  alkylene glycols, such as, for example, ethylene glycol, diethylene glycol, propylene glycol, butylene glycol, hexylene glycol, and polyethylene glycols with an average molecular weight of from 100 to 1000 Daltons;
  technical-grade oligoglycerol mixtures with a degree of self-condensation of from 1.5 to 10, such as, for example, technical-grade diglyceryl mixtures with a diglyceryl content of from 40 to 50% by weight;
  methylol compounds, such as, in particular, trimethylolethane, trimethylolpropane, trimethylol-butane, pentaerythritol and dipentaerythritol;
  short-chain alkyl glucosides, in particular those with 1 to 8 carbon atoms in the alkyl radical, such as, for example, methyl glucoside and butyl glucoside;
  sugar alcohols having 5 to 12 carbon atoms, such as, for example, sorbitol or mannitol,
  sugars having 5 to 12 carbon atoms, such as, for example, glucose or sucrose;
  amino sugars, such as, for example, glucamine;
  dialcohol amines, such as diethanolamine or 2-amino-1,3-propanediol.

Typical examples of suitable partial glycerides are mono- and/or diglycerides of C12 to C22 fatty acids with glycerol, and technical-grade mixtures thereof. For example, mention may be made of long-chain hydroxy fatty acid monoglycerides, long-chain hydroxy fatty acid diglycerides, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride.

Typical examples of suitable partial glycerides are mono- and/or diglycerides of dicarboxylic acids having 4 to 8 carbon atoms with glycerol, and technical-grade mixtures thereof. Examples which may be mentioned are tartaric acid monoglyceride, tartaric acid diglyceride, citric acid monoglyceride, citric diglyceride, malic acid monoglyceride, malic acid diglyceride, and technical-grade mixtures thereof which can also comprise small amounts of triglyceride to a subordinate degree from the preparation process.

Addition products of from 1 to 30, preferably 5 to 10 mol of ethylene oxide onto the specified partial glycerides are likewise suitable.

Hydrophilic waxes which can be used are partial esters of glycerol and/or sorbitan with unsaturated linear or saturated, branched fatty acids having 12 to 22 carbon atoms and/or hydroxycarboxylic acids having 3 to 18 carbon atoms provided they have a melting point of >30° C.
Sorbitan Esters
Sorbitan esters which can be used are, for example, the following compounds provided they have a melting point of >30° C.

Sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Addition products of from 1 to 30, preferably 5 to 10, mol of ethylene oxide onto the specified sorbitan esters are likewise suitable.

Polyglycerol Esters

Polyglycerol esters which can be used are, for example, the following compounds provided they have a melting point of >30° C.:

Typical examples of suitable polyglycerol esters are polyglyceryl-4 diisostearate/polyhydroxy-stearate/sebacate (Isolan GPS), polyglyceryl-2 dipolyhydroxystearate (Dehymuls PGPH), polyglycerol-3 diisostearate (Lameform TGI), polyglyceryl-4 isostearate (Isolan GI 34), polyglyceryl-3 oleate, diisostearoyl polyglyceryl-3 diisostearate (Isolan PDI), polyglyceryl-3 methyl glucose distearate (Tego Care 450), polyglyceryl-3 beeswax (Cera bellina), polyglyceryl-4 caprate (polyglycerol caprate T2010/90). Polyglyceryl-3 cetyl ether (Chimexane NL), polyglyceryl-3 distearate (Cremophor GS 32) and polyglyceryl polyricinoleate (Admul WOL 1403) polyglyceryl dimerate isostearate, and mixtures thereof.

Examples of further suitable polyol esters are the mono-, di- and triesters of trimethylolpropane or pentaerythritol with lauric acid, coconut fatty acid, tallow fatty acid, palmitic acid, stearic acid, oleic acid, behenic acid and the like, optionally reacted with 1 to 30 mol of ethylene oxide.

According to the invention, waxes which can be used are also fats and fat-similar substances with wax-like consistency provided they have the required melting point. These include, inter alia, fats (triglycerides), mono- and diglycerides, natural and synthetic waxes, fat and wax alcohols, fatty acids, esters of fatty alcohols and fatty acids, and also fatty acid amides or any desired mixtures of these substances.

Fats are understood as meaning triacylglycerols, i.e. the triple esters of fatty acids with glycerol. They preferably comprise saturated, unbranched and unsubstituted fatty acid radicals. These may also be mixed esters, i.e. triple esters of glycerol with different fatty acids. According to the invention, it is possible to use so-called hydrogenated fats and oils, which are obtained by partial hydrogenation. Vegetable hydrogenated fats and oils are preferred, e.g. hydrogenated castor oil, peanut oil, soya oil, rapeseed oil, cotton seed oil, sunflower oil, palm oil, palm kernel oil, linseed oil, almond oil, corn oil, olive oil, sesame oil, cocoa butter and coconut fat.

The triple esters of glycerol with $C_{12}$-$C_{60}$-fatty acids and in particular $C_{12}$-$C_{36}$-fatty acids, inter alia, are suitable. These include hydrogenated castor oil, a triple ester of glycerol and a hydroxy stearic acid, which is commercially available, for example, under the name Cutina® HR. Glycerol tristearate, glycerol tribehenate (e.g. Syncrowax® HRC), glycerol tripalmitate or the triglyceride mixtures known under the name Syncrowax® HGLC are likewise suitable, with the proviso that the melting point of the wax component or of the mixture is 30° C. or above.

Waxes which can be used according to the invention are in particular partial esters of C12 to C22 fatty acids with polyhydric alcohols, in particular with glycerol.

Waxes which can be used according to the invention are, in particular, mono- and diglycerides and mixtures of these partial glycerides. The glyceride mixtures that can be used according to the invention include the products Novata® AB and Novata® B (mixture of $C_{12}$-$C_{18}$-mono-, di- and triglycerides) and also Cutina® MD or Cutina® GMS (glyceryl stearate) marketed by Cognis Deutschland GmbH & Co. KG.

The $C_{12}$-$C_{50}$-fatty alcohols can furthermore be used as wax. Of suitability are, in particular, $C_{12}$-$C_{24}$-fatty alcohols, which can also be used in combination with the C12-C24 partial esters of polyhydric alcohols. The fatty alcohols can be obtained from natural fats, oils and waxes, such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, preference is given to saturated unbranched fatty alcohols. However, unsaturated, branched or unbranched fatty alcohols can also be used as wax component according to the invention provided they have the required melting point. According to the invention, it is also possible to use fatty alcohol cuts, as are produced in the reduction of naturally occurring fats and oils such as, for example, beef tallow, peanut oil, rapeseed oil, cotton seed oil, soya oil, sunflower oil, palm kernel oil, linseed oil, castor oil, corn oil, rapeseed oil, sesame oil, cocoa butter and coconut fat. However, it is also possible to use synthetic alcohols, e.g. the linear, even-numbered fatty alcohols of the Ziegler synthesis (Alfols®) or the partially branched alcohols from the oxo synthesis (Dobanols®). According to the invention, $C_{14}$-$C_{22}$-fatty alcohols which are marketed, for example, by Cognis Deutschland GmbH under the name Lanette® 16 ($C_{1-6}$-alcohol), Lanette® 14 ($C_{1-4}$-alcohol), Lanette® 0 ($C_{1-6}$/$C_{1-8}$-alcohol) and Lanette® 22 ($C_{18}$/$C_{2-2}$-alcohol) are particularly preferably suitable. Fatty alcohols give the compositions a drier skin feel than triglycerides and are therefore preferred over the latter.

Wax components which can be used are also $C_{14}$-$C_{40}$-fatty acids or mixtures thereof. These include, for example, myristic acid, pentadecanoic acid, palmitic acid, margaric acid, stearic acid, nonadecanoic acid, arachidic acid, behenic acid, lignoceric acid, cerotic acid, melissic acid, erucic acid and elaeostearic acid, and also substituted fatty acids, such as, for example, 12-hydroxystearic acid, and the amides or monoethanolamides of the fatty acids, this list being illustrative and nonlimiting in character.

According to the invention, it is possible to use, for example, natural vegetable waxes, such as candelilla wax, carnauba wax, Japan wax, esparto grass wax, cork wax, guaruma wax, rice germ oil wax, sugarcane wax, ouricury wax, montan wax, sunflower wax, fruit waxes such as orange waxes, lemon waxes, grapefruit wax, laurel wax (=bay berry wax), and animal waxes, such as, for example, beeswax, shellac wax, spermaceti, wool wax and uropygial grease. Within the context of the invention, it may be advantageous to use hydrogenated or hardened waxes. Natural waxes which can be used according to the invention also include the mineral waxes, such as, for example, ceresin and ozokerite, or the petrochemical waxes, such as, for example, petrolatum, paraffin waxes and microwaxes. As wax component it is also possible to use chemically modified waxes, in particular the hard waxes, such as, for example, montan ester waxes, sasol waxes and hydrogenated jojoba waxes. The synthetic waxes which can be used according to the invention include, for example, wax-like polyalkylene waxes and polyethylene glycol waxes. Vegetable waxes are preferred according to the invention.

The wax component can likewise be selected from the group of wax esters of saturated and/or unsaturated, branched and/or unbranched alkane carboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of lactides of long-chain hydroxycarboxylic acids. Examples of such esters are the $C_{16}$-$C_{40}$-alkyl stearates, $C_{20}$-$C_{40}$-alkyl stearates (e.g. Kesterwachs® K82H), $C_{20}$-$C_{40}$-dialkyl esters of dimer acids, $C_{18}$-$C_{38}$-alkylhydroxystearoyl stearates or $C_{20}$-$C_{40}$-alkyl erucates. It is also possible to use $C_{30}$-$C_{50}$-alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetearyl behenate and behenyl behenate.

In one preferred embodiment of the invention, the lipophilic phase of the dispersions comprises at least one oil body selected from the group consisting of dialkyl ethers, dialkyl carbonates, triglyceride mixtures, esters of C8-C24-fatty acids and C8-C24 fatty alcohols, polycarbonates or a mixture of these substances, silicone oils and mixtures thereof.

In one preferred embodiment of the invention, the weight ratio of lipophilic phase to emulsifier is greater than 20:1, preferably greater than 30:1, in particular greater than 40:1, in particular greater than 50:1.

The dispersions according to the invention make it possible to stably disperse large amounts of lipophilic phase relative to the amount of emulsifier used. The dispersions obtained in this way can be diluted while retaining the droplet size distribution.

In one embodiment of the invention, the dispersions comprise
30 to 55% by weight, preferably 40 to 50% by weight, of lipophilic phase
less than or equal to 3% by weight of emulsifier, in particular less than or equal to 2% by weight, preferably less than or equal to 1% by weight, of emulsifier, where the emulsifier comprises at least one acylglutamate.

In one preferred embodiment of the invention, the dispersions comprise
30 to 55% by weight, preferably 40 to 50% by weight of lipophilic phase
Less than or equal to 3% by weight of emulsifier, in particular less than or equal to 2% by weight, preferably less than or equal to 1% by weight, of emulsifier, where the emulsifier comprises more than 30% by weight, preferably more than 50% by weight, of acyl glutamate.

The dispersions according to the invention can comprise further constituents, such as, for example, preservatives, biogenic active ingredients, UV photoprotective factors, thickeners, superfatting agents, stabilizers, polymers, antioxidants, deodorants, film formers, swelling agents, insect repellants, hydrotropes, solubilizers, perfume oils, dyes etc. The amounts of the respective additives depend on the intended use.

In one embodiment of the invention, the dispersions according to the invention comprise at least one preservative as further constituent.

Suitable preservatives are, for example, phenoxyethanol, ethylhexylglycerol, formaldehyde solution, parabens, pentanediol, mixtures of phenoxyethanol and ethylhexylglycerol (as are obtainable, for example, under the trade name Euxyl PE 9010) or sorbic acid, and also the silver complexes known under the name Surfacine® and the other substance classes listed in Annex 6, part A and B of the Cosmetics Ordinance.

In one preferred embodiment of the invention, the preservative is selected from the group consisting of phenoxyethanol, formaldehyde solution, parabens, pentanediol, ethylhexylglycerol, organic acids and mixtures thereof.

In one embodiment of the invention, the dispersions according to the invention comprise at least one UV photoprotective filter as further constituent.

Suitable UV photoprotective filters are organic substances (photoprotective filters) that are crystalline or liquid at room temperature and which are able to absorb ultraviolet rays and release the absorbed energy again in the form of longer-wave radiation, e.g. heat.

UV-B filters may be oil-soluble or water-soluble. Examples of oil-soluble substances are:
3-benzylidenecamphor or 3-benzylidenenorcamphor and derivatives thereof, e.g. 3-(4-methylbenzylidene)-camphor, as described in EP 0693471 B1
4-aminobenzoic acid derivatives, preferably 2-ethylhexyl 4-(dimethylamino)benzoate, 2-octyl 4-(dimethylamino)benzoate and amyl 4-(dimethylamino)-benzoate;
esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);
esters of salicylic acid, preferably 2-ethylhexyl salicylate, 4-isopropylbenzyl salicylate, homomethyl salicylate;
derivatives of benzophenone, preferably 2-hydroxy-4-methoxybenzophenone, 2-hydroxy-4-methoxy-4'-methyl-benzophenone, 2,2'-dihydroxy-4-methoxybenzophenone;
esters of benzalmalonic acid, preferably di-2-ethylhexyl 4-methoxybenzmalonate
triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb HEB);
propane-1,3-diones, such as, for example, 1-(4-tert-butylphenyl)-3-(4'-methoxyphenyl)propane-1,3-dione;
ketotricyclo(5.2.1.0)decane derivatives, as described in EP 0694521 B1;
hexyl 2-(4-diethylamino-2-hydroxybenzoyl)benzoate (Uvinul A plus).

Suitable water-soluble substances are:
2-phenylbenzimidazole-5-sulfonic acid and the alkali metal, alkaline earth metal, ammonium, alkylammonium, alkanolammonium and glucammonium salts thereof
sulfonic acid derivatives of benzophenones, preferably 2-hydroxy-4-methoxybenzophenone-5-sulfonic acid and its salts;
sulfonic acid derivatives of 3-benzylidenecamphor, such as, for example 4-(2-oxo-3-bornylidene-methyl)benzenesulfonic acid and 2-methyl-5-(2-oxo-3-bornylidene) sulfonic acid and salts thereof.

Suitable as typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and also enamine compounds, as described in DE 19712033 A1 (BASF). The UV-A and UV-B filters can of course also be used in mixtures. Combinations that are particularly favorable according to the invention consist of the derivatives of benzoylmethane, e.g. 4-tert-butyl-4'-methoxydibenzoylmethane (Parsol 1789) and 2-ethylhexyl 2-cyano-3,3-phenycinnamate (octocrylene) in combination with esters of cinnamic acid, preferably 2-ethylhexyl 4-methoxycinnamate and/or propyl 4-methoxycinnamate and/or isoamyl 4-methoxycinnamate. Such combinations are advantageously combined with water-soluble filters, such as, for example, 2-phenylbenzimidazole-5-sulfonic acid and the alkali metal, alkaline earth metal, ammonium, alkylammonium, alkanolammonium and glucammonium salts thereof.

According to the invention, preference is given to UV photoprotective filters selected from Annex VII of the European cosmetics legislation ($24^{th}$ adapting commission directive, Feb. 29, 2000).

Besides the specified soluble substances, insoluble photoprotective pigments, namely finely disperse metal oxides or salts, are also suitable for this purpose. Examples of suitable metal oxides are, in particular, zinc oxide and titanium dioxide and in addition oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, preferably between 5 and 50 nm and in particular between 15 and 30 nm. They can have a spherical form, or where it is also possible to use those particles which have an ellipsoidal form or a form which deviates in some other way from the spherical shape. The pigments may also be present in surface-treated, i.e. hydrophilized or hydrophobicized, form. Typical examples are coated titanium dioxides, such as, for example, titanium dioxide T 805 (Degussa) or Eusolex® T2000 (Merck). Suitable hydrophobic coatings here are primarily silicones and specifically trialkoxyoctyl-silanes or simethicones. So-called micropigments or nanopigments are preferably used in sunscreen compositions. Preference is given to using micronized zinc oxide. Further suitable UV photoprotective filters can be found in the review by P. Finkel in SÖFW Journal 122, 543 (1996) and Parf. Kosm. 3, 11 (1999).

Besides the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cystein, cystine, cystamine and the glycosyl, N-acetyl, methyl, ethyl, propyl, amyl, butyl and lauryl, palmitoyl, oleyl, linoleyl, cholesteryl and glyceryl esters thereof), and also salts thereof, dilauryl thiodipropionate, distearyl thiodipropionate, thiodipropionic acid and derivatives (esters, ethers, peptides, lipids, nucleotides, nucleosides and salts) thereof, and also sulfoximine compounds (e.g. buthionine sulfoximines, homocystein sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg-ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydro-guaiacic acid, nordihydroguaiaretic acid, trihydroxybutyrophenone, uric acid and derivatives thereof, mannose and derivatives thereof, super oxide dismutase, zinc and derivatives thereof (e.g. ZnO, ZnSO4), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

In one embodiment of the invention, the dispersions according to the invention comprise at least one biogenic active ingredient as further constituent.

Biogenic active ingredients are understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as, for example, prune extract, bambara nut extract and vitamin complexes.

In one preferred embodiment of the invention, the dispersions according to the invention comprise at least one compound selected from vitamins, allantoin, bisabolol and plant extracts as biogenic active ingredient.

In one preferred embodiment of the invention, the dispersions according to the invention comprise at least one compound selected from tocopherol, tocopherol acetate, tocopherol palmitate, ascorbic acid, β-glucans, retinol, bisabolol, allantoin, phytantriol, panthenol, AHA acids, plant extracts and mixtures thereof as biogenic active ingredient.

In one embodiment of the invention, the dispersions according to the invention comprise at least one thickener as further constituent.

Suitable thickeners are, for example, Aerosil grades (hydrophilic silicas), polysaccharides, in particular xanthan gum, guar guar, agar-agar, alginates and tyloses, carboxymethylcellulose and hydroxyethyl- and hydroxypropylcellulose, polyvinyl alcohol, polyvinylpyrrolidone and bentonites, such as, for example, Bentone® Gel VS-5PC (Rheox).

In one embodiment of the invention, the dispersions according to the invention comprise at least one deodorizing active ingredient as further constituent. Deodorizing active ingredients counteract, conceal or eliminate body odors. Body odors are formed as a result of the action of skin bacteria on apocrine perspiration, with the formation of degradation products which smell unpleasant. Accordingly, suitable deodorizing active ingredients are, inter alia, antimicrobial agents, enzyme inhibitors, odor absorbers or odor concealers.

Suitable insect repellents are, for example, N,N-diethyl-m-toluamide, 1,2-pentanediol or ethyl 3-(N-n-butyl-N-acetylamino)propionate, which is sold under the name Insect Repellent® 3535 by Merck KGaA, and also butyl acetylaminopropionate.

A suitable self-tanning agent is dihydroxyacetone. Suitable tyrosine inhibitors, which prevent the formation of melanin and are used in depigmentation compositions, are, for example, arbutin, ferulic acid, kojic acid, coumaric acid and ascorbic acid (vitamin C).

Dyes which can be used are the substances approved and suitable for cosmetic purposes. Examples are cochenille red A (C.I. 16255), patent blue V (C.I. 42051), indigotin (C.I. 73015), chlorophylin (C.I. 75810), quinoline yellow (C.I. 47005), titanium dioxide (C.I. 77891), indanthrene blue RS(C.I. 69800) and madder lake (C.I. 58000). These dyes are usually used in concentrations of from 0.001 to 0.1% by weight, based on the total mixture.

Perfume oils which may be mentioned are mixtures of natural and synthetic fragrances. Natural fragrances are extracts from flowers, stems and leaves, fruits, fruit peels, roots, woods, herbs and grasses, needles and branches, resins and balsams. Also suitable are animal raw materials, such as, for example, cibet and castoreum, and also synthetic fragrance compounds of the ester, ether, aldehyde, ketone, alcohol and hydrocarbon type.

Further constituents of the dispersion (such as, for example, preservatives, cosmetic active ingredients, UV filters etc.) are added to the dispersion either via the water phase or via the lipophilic phase, depending on their solubility.

Preparation of the Dispersions According to the Invention

The dispersions according to the invention are prepared by homogenization of the immiscible phases. The homogenization or dispersion takes place, if appropriate, at temperatures greater than room temperature. In this case, the dispersion is cooled again to room temperature after the dispersion process.

In dispersion technology, homogenization is understood as meaning the very fine comminution of the disperse phase of a crude emulsion. In the case of the liquid/liquid dispersion, the droplet size spectrum of the crude emulsion shifts significantly toward smaller drops. As a result of the drop comminution, new phase boundaries are formed which have to be rapidly completely coated by emulsifier molecules since, in so doing, the newly formed drop is better stabilized and, on account of the low interfacial tension, can be further comminuted more easily.

The dispersions according to the invention can be obtained by customary emulsifying techniques. The invention relates to a process for the preparation of the dispersions according to the invention in which the water phase and also the mixture comprising emulsifier and the lipophilic phase are combined and the homogenization is carried out with an energy input of $1 \times 10^5$ to $2 \times 10^3$ J/m$^3$.

The homogenization apparatuses used may be high-pressure dispersion systems, such as, for example, radial diffusers with flat valve or toothed valve; counterflow dispersers, such as, for example, microfluidizer; jet dispersers or orifice systems. Suitable dispersion systems are also rotor-stator systems, ultrasound systems, ball mills or membranes.

When using high-pressure dispersing systems as homogenization apparatus, pressures of from 50 to 2500 bar, preferably 200 to 800 bar and in particular 400 to 600 bar, are used.

In the case of emulsion preparation by means of micromixers, a pressure range from 2 to 30, preferably from 5 to 20 bar, is customary. Micromixers have the advantage of producing finely divided and narrow particle size distributions at low pressures in a particularly gentle manner.

In one preferred embodiment of the process according to the invention, the homogenization is carried out by means of high-pressure homogenization.

The advantage of high-pressure homogenization is that small droplets with a very narrow size distribution are very readily formed, which is advantageous if low viscosity dispersions are to be prepared with phase stability. On account of the applications-related advantages of an emulsion prepared by high-pressure homogenization, it is increasingly attempted to also use such homogenization techniques in the cosmetics industry. On account of the fact that a new interface is formed particularly rapidly, high requirements are to be placed on emulsifier and carrier phase since the emulsifiers must coat the interface spontaneously and very rapidly in order to ensure optimum phase stability.

In order to achieve finely divided dispersions with a monomodal and narrow particle size distribution, in particular with a WDS value of less than or equal to 2, it may be advantageous to combine different emulsifying processes with one another. In a stirred container, for example, a predispersion can be prepared, which is then homogenized by dispersion in a so-called single passage by means of a rotor-stator system and then by means of a high-pressure homogenizer. Single passage is to be understood here as meaning a procedure in which the entire contents of a container is passed once through the homogenization apparatus to another container. In contrast to the so-called circulation procedure, this ensures that every liquid element has passed through the homogenization apparatus. No coarse emulsion droplets are left behind which can form the starting point for the disintegration of the dispersion.

Rotor-stator systems are preferably used for the predispersion. Rotor-stator systems may be apparatuses such as toothed colloid mills or machines which consist of one or more rotors and stators with passage openings in the form of slits or cylindrical or rectangular holes, such as, for example, of the Cavitron, Supraton, Siefer, Bran+Lübbe, IKA, Koruma, Silverson type etc.

In one preferred embodiment of the invention, the homogenization step or steps is/are passed through several times.

In one embodiment of the invention, the dispersions according to the invention can be produced by preparing concentrates and subsequently diluting them with water. This may be advantageous particularly in the case of dispersions with a low end concentration of lipophilic phase.

INDUSTRIAL APPLICABILITY

The dispersions according to the invention are suitable for use in cosmetic and/or pharmaceutical preparations. Examples are sprayable dispersions for bodycare (deodorant sprays, sunscreen sprays etc.), care products in gel or cream form, medicament-containing sprays, gels, or creams, impregnated care wipes or pads (make-up removers, cleaning wipes etc.) and the like.

The invention thus further relates to the use of the dispersions according to the invention in cosmetic and/or pharmaceutical preparations, in particular for producing cosmetic and/or pharmaceutical preparations.

The dispersions are particularly suitable for application to papers, wipes, textiles and cotton wool products which are used in the field of babycare and baby hygiene, and also in the field of make-up removal, in particular eye make-up removal, in the field of womens hygiene (tampons, sanitary towels, panty liners) and in the field of body hygiene (toilet paper, moist toilet paper).

Standard commercial cleaning wipes are impregnated either with aqueous lotions based on ethoxylate-containing (EO) emulsifiers, as described, for example, in WO 00/04230, or else with aqueous, clear solubilizates. On account of the EO content, the first-mentioned aqueous lotions are not accepted in various market places (ecoconformity). By con trast, the clear solubilizates are often very sticky and sensorially unacceptable. Since, on account of the stickiness, very heavy dilutions of solubilizates have to be used, the wipes produced therewith only have a low cleaning power. The dispersions according to the invention comprise small amounts of emulsifier and large amounts of oil and wax. They therefore have a very high cleaning power. In addition, in one preferred embodiment, the dispersions comprise no ethoxylated emulsifiers.

The application therefore further relates to the use of the dispersions according to the invention on papers, nonwovens and wovens, in particular the use for the application to or finishing of papers, nonwovens and wovens. According to the invention, these include all types of paper, nonwovens and wovens which are known to the person skilled in the art and products which can be produced therefrom, such as, for example, toilet paper, paper handkerchiefs, tissues, wipes, cotton wool, cotton wool pads, make-up removers, tampons, sanitary towels, panty liners, diapers, babycare wipes, baby cleaning wipes, textiles, etc. The application likewise relates to paper, nonwoven and woven products for bodycare and body cleaning which comprise a dispersion according to the invention.

Examples of substrates of these paper, nonwoven and woven products which may be mentioned are: carriers made of textile fiber, e.g. of natural fiber, such as cellulose, silk, wool, regenerated cellulose (viscose, rayon), cellulose derivatives and/or synthetic fibers, such as, for example, polyester, polypropylene, polyethylene terephthalate, polyamine, polyolefin, polyacrylonitrile fibers or mixtures of such fibers, woven or nonwoven.

The products according to the invention can be produced by methods known to the person skilled in the art. The application of the dispersions according to the invention to the paper, nonwoven and woven products according to the invention for bodycare and body cleaning is carried out here according to methods known to the person skilled in the art, such as, for example, impregnation, saturation, immersion, spraying, scrapping or coating. This can be carried out either at room temperature or else at elevated temperatures. The dispersion according to the invention can be diluted prior to application to the paper, nonwoven and woven substrate and, if appropriate, the resulting paper, nonwoven and woven product can then be dried.

The invention relates to a paper, nonwoven and/or woven product for bodycare and/or for body cleaning which comprises 0.5 to 70% by weight of active substance of the dispersion, based on the total weight of the product.

In one preferred embodiment of the invention, the paper, nonwoven and/or woven products comprise more than 2% by weight, in particular more than 3% by weight, particularly preferably more than 4% by weight, in particular more than 5% by weight, of active substance of the dispersion, based on the total weight of the product.

In one preferred embodiment of the invention, the paper, nonwoven and/or woven products comprise 10 to 60% by weight, in particular 15 to 50% by weight, preferably 20 to 45% by weight, of active substance of the dispersion, based on the total weight of the product.

Active substance of the dispersion is understood as meaning all of the constituents of the dispersion minus the water.

The paper, nonwoven or woven products can be after-treated in a drying step in order to reduce the water content after the spray application or in order to obtain virtually water-free products (e.g. dry wipes). In one embodiment of the invention, paper, nonwoven and woven products coated according to the invention are subsequently subjected to a drying step.

The invention further relates to the use of the dispersions according to the invention on paper, nonwovens and/or wovens, in particular as impregnating agents and/or hand-modifying agents.

Furthermore, it has surprisingly been established that dispersions comprising phospholipids, in particular lecithins, increase the care feel on the skin which comes into contact with the paper, nonwoven and woven products.

Furthermore, it has surprisingly been found that dispersions comprising phospholipids, in particular lecithins, increase the soft handle of the paper, nonwoven and woven products.

EXAMPLES

Preparation of the Dispersion (Emulsion) According to Table 1, Example 12

20 g of Cetiol™ SN (INCI: Cetearyl Isononanoate), 5 g of Cutina™ PES (INCI: Pentaerythrityl Distearate), 3 g of glycerol and 2 g of Leciprime™ 1800 IP (INCI: Lecithin, manufacturer Cargill) were dissolved or predispersed at 60° C. in a beaker with stirring. In a second beaker, 1 g of acyl glutamate (Eumulgin™ SC) was dissolved in 60° C.-hot distilled water. The preservative Uniphen P-23 (manufacturer Induchem) was added to this aqueous phase. The oil phase was added to the aqueous phase with stirring and prehomogenized at 5200 rpm for 2 minutes with the help of an Ultra Turrax (IKA model T50, tool S50N-G40G). The pre-emulsion was then homogenized in a further homogenization step using a high-pressure homogenizer (APV, LAB 60) at 750 bar. This homogenization step was passed through a total of 5×. Table 1 shows dispersions (emulsions) according to the invention, Examples 1 to 20.

Storage Experiments

To investigate the storage stability (phase stability) of the dispersions according to the invention, they were stored at room temperature (23° C.) and at 45° C. for 6 weeks. Dilute dispersions were likewise prepared by diluting the dispersions with water to a dispersion content of 10% by weight.

The drop/particle size distribution of the undiluted and of the diluted dispersions was determined before, during and after the storage experiments, the resulting $d_{90}$ value and the appearance of the dispersions were used to assess the storage stability.

The d value (more accurately $d_{3,90}$ value) obtained in this way describes that 90% of the volume of the disperse (emulsified) phase is formed from drops with a diameter of $<=d_{3,90}$.

The particle size distribution was determined using an instrument from Beckmann Coulter, model LS 230, using the optical model emulsion d.rfd PIDS included (from 14.8.2001) in accordance with the operating instructions (1994). The measurement medium used was water. The particle size was measured directly after preparing the dispersions and in the course of the storage experiments. According to the information from the manufacturer of the instrument, in each case dilute dispersions were measured, i.e. a sufficient amount of the dispersions was stirred into distilled water until the instrument-specific saturation concentration was indicated by the instrument. Table 2 shows the results for these storage experiments.

TABLE 1

| | | Examples | | | | | | | | | | |
|---|---|---|---|---|---|---|---|---|---|---|---|---|
| | | 1 | 2 | 3 | 4 | 5 | 6 | 7 | 8 | 9 | 10 | 11 |
| Dist. Water | [%] | 71.0 | 69.0 | 66.0 | 73.25 | 60.75 | 66.75 | 58.75 | 71.75 | 69.75 | 67.7 | 65.7 |
| Water with citric acid to pH 5.5 | [%] | — | — | — | — | — | — | — | — | — | — | — |
| Leciprime 1800 IP | [%] | — | — | — | — | 6.0 | — | — | — | — | 2.0 | 4.00 |
| Soluthin MD | [%] | — | — | — | — | — | — | — | — | 6.00 | — | — |
| Phosal 50 SA+ | [%] | — | — | — | — | — | — | — | 4.00 | — | — | — |
| Lipoid SL 80-3 | [%] | — | 2.00 | — | — | — | — | 6.00 | — | — | — | — |
| Cutina CP | [%] | 5.00 | 5.00 | 10.00 | 0.75 | 0.75 | 0.75 | 0.75 | 0.75 | 0.75 | 5.00 | 5.00 |
| Cetiol CC | [%] | — | — | — | — | — | — | — | — | — | — | — |
| Cetiol SN | [%] | 20.00 | 20.00 | 20.00 | 20.00 | 20.00 | 20.00 | 20.00 | 20.00 | 20.00 | 20.00 | 20.00 |
| Cutina PES | [%] | — | — | — | — | — | — | — | — | — | — | — |
| Myritol 318 | [%] | — | — | — | — | — | — | — | — | — | — | — |
| Cutina GMS | [%] | — | — | — | — | — | — | — | — | — | — | — |
| Glycerol | [%] | 3.00 | 3.00 | 3.00 | 3.00 | 11.50 | 11.50 | 11.50 | 3.00 | 3.00 | 3.00 | 3.00 |
| Eumulgin SG | [%] | 1.00 | 1.00 | 1.00 | — | 1.00 | 1.00 | — | 0.50 | 0.50 | 1.00 | 1.00 |
| Plantapon ACG 35 | [%] | — | — | — | 3.00 | — | — | 3.00 | — | — | — | — |
| Uniphen P-23 | [%] | — | — | — | — | — | — | — | — | — | 1.30 | 1.30 |
| Pressure | [bar] | 750/50[1] | 750/50[1] | 750/50[1] | 750/50[1] | 750/50[1] | 750/50[1] | 750/50[1] | 750/50[1] | 750/50[1] | 750/50[1] | 750/50[1] |
| Particle diameter $d_{90}$ | [nm] | 206 | 195 | 193 | 184 | 223 | 185 | 190 | 193 | 183 | 177 | 189 |
| Sauter diameter $d_{3,2}$ | [nm] | 141 | 144 | 145 | 140 | 123 | 140 | 140 | 147 | 142 | 135 | 145 |
| WDS | | 0.705 | 0.561 | 0.530 | 0.517 | 1.076 | 0.497 | 0.549 | 0.507 | 0.476 | 0.515 | 0.507 |

| | | 12 | 13 | 14 | 15 | 16 | 17 | 18 | 19 | 20 |
|---|---|---|---|---|---|---|---|---|---|---|
| Dist. Water | [%] | 67.7 | 69.7 | 67.7 | 69.7 | 69.7 | — | — | — | — |
| Water with citric acid to pH 5.5 | [%] | — | — | — | — | — | 67.7 | 67.7 | 57.2 | 44.7 |
| Leciprime 1800 IP | [%] | 2.00 | — | 2.00 | — | 2.00 | 2.00 | 2.00 | — | — |
| Soluthin MD | [%] | — | — | — | — | — | — | — | — | — |
| Phosal 50 SA+ | [%] | — | — | — | — | — | — | — | — | — |
| Lipoid SL 80-3 | [%] | — | — | — | — | — | — | — | — | — |
| Cutina CP | [%] | — | — | 5.00 | 5.00 | — | — | — | — | — |
| Cetiol CC | [%] | — | — | 5.00 | 5.00 | — | — | — | — | — |
| Cetiol SN | [%] | 20.00 | 20.00 | 10.00 | 10.00 | 20.0 | 20.0 | 20.00 | 30.0 | 40.0 |
| Cutina PES | [%] | 5.00 | 5.00 | — | — | — | 5.00 | 5.00 | 7.50 | 10.0 |
| Myritol 318 | [%] | — | — | 5.00 | 5.00 | — | — | — | — | — |
| Cutina GMS | [%] | — | — | — | — | 5.00 | — | — | — | — |
| Glycerol | [%] | 3.00 | 3.00 | 3.00 | 3.00 | 3.00 | 3.00 | 3.00 | 3.00 | 3.00 |
| Eumulgin SG | [%] | 1.00 | 1.00 | 1.00 | 1.00 | 1.00 | 1.00 | 1.00 | 1.00 | 1.00 |
| Plantapon ACG 35 | [%] | — | — | — | — | — | — | — | — | — |
| Uniphen P-23 | [%] | 1.30 | 1.30 | 1.30 | 1.30 | 1.30 | 1.30 | 1.30 | 1.30 | 1.30 |
| Pressure | [bar] | 750/50[1] | 750/50[1] | 750/50[1] | 750/50[1] | 750/50[1] | 750/50[1] | 430/50[1] | 450/50[1] | 450/50[1] |
| Particle diameter $d_{90}$ | [nm] | 159 | 156 | 174 | 167 | 149 | 149 | 194 | 192 | 197 |
| Sauter diameter $d_{3,2}$ | [nm] | 120 | 119 | 130 | 128 | 112 | 137 | 150 | 150 | 152 |
| WDS | | 0.530 | 0.509 | 0.541 | 0.500 | 0.54 | 0.479 | 0.49 | 0.464 | 0.484 |

[1] All of the examples were carried out using the high-pressure homogenizer APV, LAB 60, the homogenization was carried out 5x, in Example 5 the homogenization was only carried out 2x.

TABLE 2

Storage experiments of selected formulations

| | | Example No. | | | | | | | | |
|---|---|---|---|---|---|---|---|---|---|---|
| | | 5 | 6 | 8 | 10 | 12 | 13 | 14 | 15 | 16 |
| $d_{90}$ original emulsion start | [nm] | 223 | 185 | 199 | 184 | 163 | 158 | 181 | 172 | 157 |
| $d_{90}$ dilute emulsion start | [nm] | 223 | 184 | 198 | 184 | 162 | 159 | 181 | 172 | 156 |
| $d_{90}$ original emulsion 6 weeks at RT | [nm] | 224 | 185 | 198 | 189 | 166 | 166 | 184 | 177 | 160 |
| $d_{90}$ original emulsion 6 weeks at 45° C. | [nm] | 224 | 189 | 187 | 190 | 168 | 168 | 186 | 181 | 159 |
| $d_{90}$ dilute emulsion 6 weeks at RT | [nm] | 223 | 185 | 198 | 190 | 166 | 165 | 187 | 176 | 159 |
| $d_{90}$ dilute emulsion 6 weeks at 45° C. | [nm] | 223 | 187 | 186 | 190 | 166 | 167 | 189 | 179 | 159 |

TABLE 2-continued

Storage experiments of selected formulations

| | Example No. | | | | | | | | |
|---|---|---|---|---|---|---|---|---|---|
| | 5 | 6 | 8 | 10 | 12 | 13 | 14 | 15 | 16 |
| Appearance | | | | | | | | | |
| $d_{90}$ original emulsion start | thin-liquid, no separation | | | | | | | | |
| $d_{90}$ dilute emulsion start | thin-liquid, no separation | | | | | | | | |
| $d_{90}$ original emulsion 6 weeks at RT | thin-liquid, no separation | | | | | | | | |
| $d_{90}$ original emulsion 6 weeks at 45° C. | thin-liquid, no separation | | | | | | | | |
| $d_{90}$ dilute emulsion 6 weeks at RT | thin-liquid, no separation | | | | | | | | |
| $d_{90}$ dilute emulsion 6 weeks at 45° C. | thin-liquid, no separation | | | | | | | | |

Sensory Evaluation

To evaluate the sensory properties of the emulsions according to the invention, 20% strength by weight dilutions of Examples 12 and 13 (see Table 1) were prepared with water. In each case, 5 g of these dilutions were applied to wipes (spun lace, 180 mm×200 mm, 55 gsm, 65% viscose rayon/ 35% polyester) and assessed in sensory terms by an expert panel consisting of 12 people according to the following criteria:
- softness 1=assessment how soft or rough the wipe feels overall in the hand
- softness 2=assessment how soft or rough the wipe feels upon contact with the forearm
- stickiness
- harshness
- care feel The assessment was made using grades from 1 to 7, with grade 1 meaning "a little", and grade 7 meaning "a lot".

Examples 12 and 13 from Table 1 were thus assessed:

| Criterion | Example 12 | Example 13 |
|---|---|---|
| Softness 1 | 7 | 5 |
| Softness 2 | 7 | 5 |
| Stickiness | 2 | 3 |
| Harshness | 1 | 3 |
| Care feel | 7 | 5 |

The examples show that the good sensory properties already achieved with the dispersion according to the invention (Example 13) can be further improved through the addition of lecithin (Example 12).

What is claimed is:

1. A dispersion consisting essentially of:
   (a) water,
   (b) a lipophilic phase,
   (c) an emulsifier consisting essentially of more than about 30% by weight of at least one acylglutamate, wherein said emulsifier is less than or equal to about 3% by weight based on the total weight of the dispersion, and;
   (d) optionally, at least one phospholipid.

2. The dispersion of claim 1, wherein said emulsifier includes less than about 10% by weight of ethoxylated emulsifiers.

3. The dispersion of claim 1, wherein the dispersion has a size distribution of dispersed particles of Sauter diameter D[3,2] less than or equal to about 400 nm.

4. The dispersion of claim 1, wherein said phospholipid comprises at least one lecithin.

5. A process for the preparation of dispersions of claim 1, comprising
   (a) combining an aqueous phase and a lipophilic/emulsifier phase to form a mixture, and
   (b) homogenizing said mixture with an energy input of from about $1\times10^5$ to about $2\times10^8$ J/m$^3$.

6. The dispersion of claim 1, wherein said emulsifier consists essentially of more than about 50% by weight of at least one acylglutamate.

7. The dispersion of claim 1, wherein said emulsifier includes less than about 5% by weight of ethoxylated emulsifiers.

8. The dispersion of claim 1, wherein the dispersion has a size distribution of dispersed particles of Sauter diameter D[3,2] less than or equal to about 200 nm.

9. A method of preparing cosmetic and/or pharmaceutical preparations comprising adding the dispersion of claim 1 to a cosmetic and/or pharmaceutical formulation.

10. A method of impregnating papers, nonwovens and/or wovens comprising adding the dispersion of claim 1 to papers, nonwovens and/or wovens.

11. A paper, nonwoven or woven product comprising the dispersion of claim 1, wherein the resulting paper, nonwoven or woven product is useful for bodycare and/or for cleaning the body.

* * * * *

UNITED STATES PATENT AND TRADEMARK OFFICE
CERTIFICATE OF CORRECTION

PATENT NO. : 8,357,381 B2
APPLICATION NO. : 12/298687
DATED : January 22, 2013
INVENTOR(S) : Rainer Eskuchen et al.

Page 1 of 1

It is certified that error appears in the above-identified patent and that said Letters Patent is hereby corrected as shown below:

Claim 1, column 24, line 18, "optionally," should be removed.

Signed and Sealed this
Nineteenth Day of March, 2013

Teresa Stanek Rea
*Acting Director of the United States Patent and Trademark Office*